United States Patent
Ashman

(10) Patent No.: US 6,554,803 B1
(45) Date of Patent: *Apr. 29, 2003

(54) COMBINATION SYRINGE AND ASPIRATOR FOR BONE REGENERATION MATERIAL AND METHOD FOR USING THE SYRINGE

(76) Inventor: Arthur Ashman, P.O. Box 3068, Westport, CT (US) 06880

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/086,604

(22) Filed: May 29, 1998

Related U.S. Application Data

(62) Division of application No. 08/831,914, filed on Apr. 2, 1997.

(51) Int. Cl.⁷ ............................................. A61M 37/00
(52) U.S. Cl. .......................... 604/218; 433/90; 433/89; 604/243
(58) Field of Search ................................ 604/181, 187, 604/218, 190, 239, 240, 243, 275, 276, 278, 264, 285, 540, 57, 59, 60, 61, 68, 73, 77, 82, 85, 92; 600/573, 576, 578, 579; 606/86, 92, 93, 94; 433/80, 83, 87, 89, 90, 215

(56) References Cited

U.S. PATENT DOCUMENTS 2,857,913 A * 10/1958 Miskel ........................ 604/190
4,061,143 A * 12/1977 Ishikawa .................... 604/190

(List continued on next page.)

FOREIGN PATENT DOCUMENTS

| FR | 2494580 | * 5/1982 | .................. 433/89 |
| WO | WO 98/16268 | 4/1998 | ........... A61L/27/00 |

Primary Examiner—Anhtuan T. Nguyen
Assistant Examiner—Ann Y Lam
(74) Attorney, Agent, or Firm—Darby & Darby

(57) ABSTRACT

An improved assembly of a syringe and a nozzle tip for aspirating marrow blood from a surgical site and a method for using this improved syringe. The syringe includes a nozzle tip of special construction which has a sleeve portion, which fits on the free end of the barrel of the syringe, and a curved aspirating nozzle end. The nozzle tip includes a filter screen of preselected mesh size. A sufficient amount of marrow blood is aspirated through the curved aspirating nozzle end and the filter screen of the nozzle tip, thereby moving a preselected amount of marrow blood into the barrel of the syringe. The aspirated marrow blood then mixes with the granules of bone regeneration material disposed in the barrel of the syringe to form a viscous fluid mixture therein. The excess marrow blood, if any, is expelled through the curved aspirating nozzle end by applying a moderate manual pressure to the plunger of the syringe. After visual inspection of the formed viscous fluid mixture in the syringe, the nozzle tip is then manually removed from the syringe and the viscous fluid mixture is applied to a surgical site by applying manually pressure on the plunger of the syringe. The filter screen is mounted inside a flange adjoining the sleeve portion in the nozzle tip. This filter screen has openings of predetermined mesh size to prevent the granules of bone regeneration material from exiting through the nozzle tip during the aspirating of the marrow blood into the syringe barrel and prior to the removal of the nozzle from the syringe barrel and the expelling of the viscous mixture to a surgical site.

11 Claims, 3 Drawing Sheets

U.S. PATENT DOCUMENTS

| | | | | |
|---|---|---|---|---|
| 4,127,131 A | * | 11/1978 | Vaillancourt | 604/190 |
| 4,192,305 A | | 3/1980 | Seberg | |
| 4,199,864 A | | 4/1980 | Ashman | 433/175 |
| 4,244,689 A | | 1/1981 | Ashman | 433/175 |
| 4,366,822 A | | 1/1983 | Altschuler | 128/753 |
| 4,535,485 A | | 8/1985 | Ashman et al. | 623/16 |
| 4,536,158 A | | 8/1985 | Bruins et al. | 433/201.1 |
| 4,547,327 A | | 10/1985 | Bruins et al. | 264/16 |
| 4,547,390 A | | 10/1985 | Ashman et al. | 427/2 |
| 4,569,662 A | * | 2/1986 | Dragan | 433/89 |
| 4,728,570 A | | 3/1988 | Ashman et al. | 428/327 |
| 4,751,921 A | * | 6/1988 | Park | 606/93 |
| 4,784,607 A | * | 11/1988 | Francois | 433/89 |
| 4,834,706 A | | 5/1989 | Beck et al. | |
| 4,859,336 A | * | 8/1989 | Savas et al. | 604/190 |
| 4,902,421 A | * | 2/1990 | Pascale et al. | 604/190 |
| 4,911,641 A | | 3/1990 | Detsch | 433/228 |
| 5,026,283 A | * | 6/1991 | Osanai et al. | 433/90 |
| 5,181,918 A | * | 1/1993 | Brandhorst et al. | 606/92 |
| 5,267,859 A | * | 12/1993 | Discko, Jr. | 433/89 |
| 5,269,785 A | | 12/1993 | Bonutti | 606/80 |
| 5,324,273 A | * | 6/1994 | Discko, Jr. | 433/90 |
| 5,330,357 A | | 7/1994 | Keller | 433/215 |
| 5,824,087 A | | 10/1998 | Aspden | 623/16 |

* cited by examiner

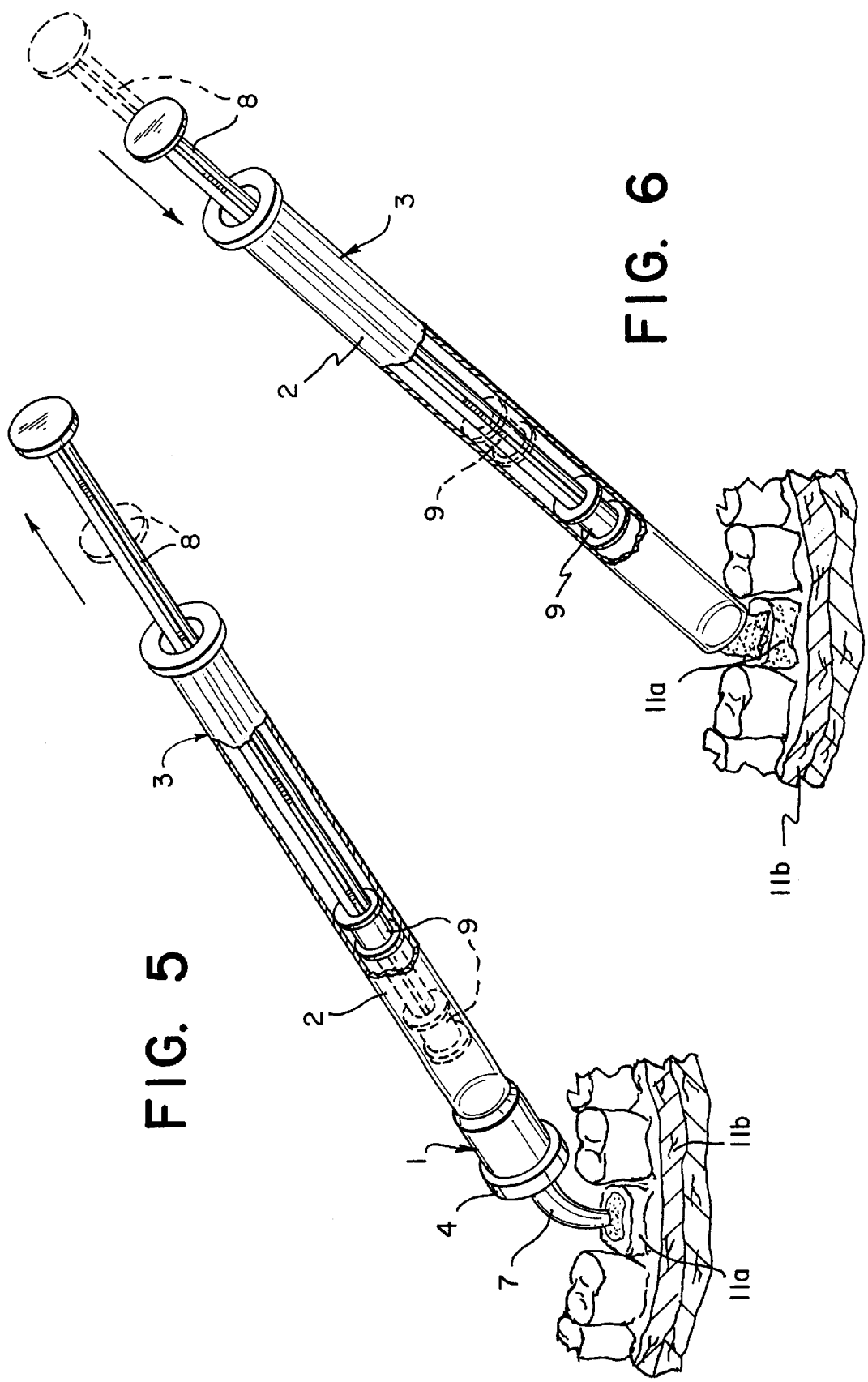

COMBINATION SYRINGE AND ASPIRATOR FOR BONE REGENERATION MATERIAL AND METHOD FOR USING THE SYRINGE

This is a divisional application of application Ser. No. 08/831,914 filed Apr. 2, 1997, now pending.

BACKGROUND OF THE INVENTION

The invention relates to a nozzle tip of special construction mounted an the barrel of a standard syringe for dispensing bone regeneration materials to a surgical site. The nozzle tip and syringe are used to aspirate marrow blood from a surgical site; then mixing the collected blood marrow with granular bone regeneration material stored in the barrel of the syringe to form a viscous fluid mixture therein; then manually removing the nozzle tip from the syringe barrel; and then dispensing the viscous fluid mixture to the surgical site by manual application of pressure on the plunger of the syringe. Bone regeneration materials are known in the art. For example, hard-tissue implant materials are known, such as the calcified microporous co-polymer bone regeneration material marketed under the trademarks Bioplant® HTR® Synthetic Bone™ alloplast. The aforesaid bone regeneration material has been widely accepted in medicine, dentistry and veterinary medicine as a prostethic bone material to repair injured or diseased bone. The followig co-invented U.S. patents describe the use of such bone generation materials: U.S. Pat. Nos. 4,199,864; 4,244,689; 4,535,485; 4,536,158; 4,547,327; 4,547,390 and 4,728,570. The aforelisted co-invented U.S. patents are incorporated by reference herein. For many applications of said Bioplant®, HTR® bone regeneration material the application of this material in granular form has proven to have many advantages. For example, granular Bioplant®, HTR® bone regeneration material has proven particularly useful in a tooth extraction procedure. A simple injection of granular Bioplant®, HTR® bone regeneration material into the tooth socket, following immediately after extraction of the tooth, either significantly reduces or completely prevents the usual 40% to 60% percent bone loss that otherwise occurs within 2–3 years after tooth extraction, and eliminates much of the pain and inflammation of the tooth socket (post-extraction alveolar osteitis). Granular Bioplant®, HTR® bone regeneration material works best when it is thoroughly wetted with marrow blood before being applied to a surgical site.

SUMMARY OF THE INVENTION

It is an object of the present invention to provide a simple improved syringe and nozzle tip construction for producing and then dispensing a viscous mixture of granular Bioplant®, HTR® bone regeneration material and marrow blood, obtained from a surgical site.

It is another object of the invention to provide a simple method of mixing aspirated marrow blood from a surgical site with granular bone regeneration material inside the barrel of a syringe and, by the use of an improved nozzle tip construction, mounted on a standard syringe, prevent excessive loss of marrow blood and/or granular bone regeneration material during the mixing operation.

It is another object of this invention to provide an aseptic method for mixing aspirated marrow blood from a surgical site with granular bone regeneration material and then applying, in an aseptic manner, the viscous mixture obtained by the mixing in the sterile syringe barrel to the surgical site.

Low density polyethylene has been found to be particularly advantageous for manufacturing the entire nozzle tip construction including the filter screen which is mounted inside the nozzle tip. The openings of the mesh screen must be smaller than the grain size of the granular bone regeneration material inside the syringe barrel. A mesh opening size of about 105 microns has been found to work best with the method of the invention because it can be used with several standard granular sizes of Bioplant®, HTR® bone regeneration materials.

Further details regarding the nozzle tip construction and the method of forming a viscous mixture of granular Bioplant® HTR® polymer material and then applying it to a surgical site will be provided in the followig description of preferred embodiments in conjunction with the accompanying drawings.

BRIEF DESCRIPTION OF THE DRAWINGS

FIG. 5 is a view in perspective showing the step of aspirating marrow blood from a tooth socket with the nozzle tip construction of the invention; and FIG. 6 is a view in perspective showing the step of applying the viscous in the syringe barrel to the tooth socket.

DESCRIPTION OF THE PREFERRED EMBODIMENTS

Although the principles of this invention are applicable to other surgical procedures than a tooth extraction, the invention will be fully understood from an explanation of its application to a preferred embodiment of a syringe and special nozzle tip construction as illustrated in FIGS. 1–6.

Figure 1:
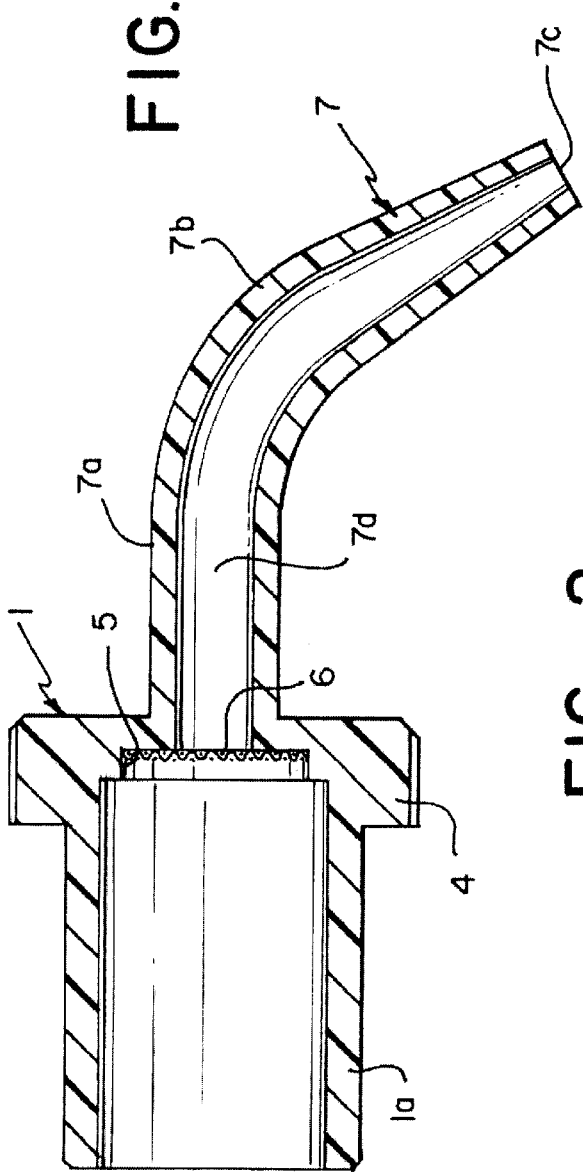
FIG. 1 is a cross-sectional view of the nozzle tip of the invention.

Shown in FIG. 1 is a cross-sectional view of the nozzle tip 1 of this invention. The nozzle tip 1 includes a sleeve portion 1a which has an internal diameter which corresponds to the external diameter of the barrel 2 of the syringe 3 illustrated in FIG. 2. The nozzle tip 1 is therefore mounted on the syringe barrel 2 by means of a friction fit. The syringe 3 is of the type that is commonly used for dispensing granular bone regeneration material, such as Bioplant®, HTR® bone regeneration material. The nozzle tip has a flange 4 which has a recess 5. A screen 6 having a mesh size of about 105 microns is mounted inside the recess 5. The nozzle tip further has a neck portion 7 with a passage 7d extending therethrough. The neck portion 7 includes an axially straight portion 7a extending from the flange 4 and integral therewith, and a curved portion 7b through the opening 7c thereof the marrow blood can be aspirated. The neck portion 7 is integral with the flange 4 and the entire nozzle tip construction including the neck portion 7 and screen 6 are preferably made by a known molding operation of low density polyethylene.

Figure 2:
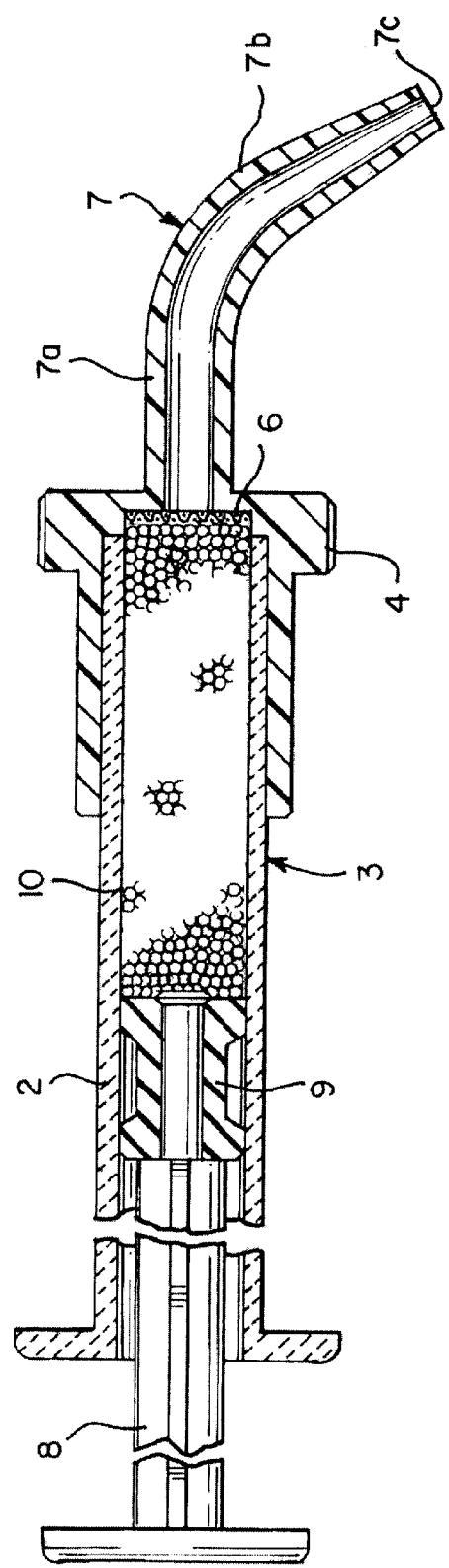
FIG. 2 is a cross-sectional view of a standard straight barrel syringe holding bone regeneration material, with a nozzle tip of the invention mounted thereon, which standard type of syringe is commonly used in applying bone regeneration materials to a surgical site.

FIG. 2 illustrates in cross-section a syringe 3 with the nozzle tip 1 mounted thereon. The barrel 2 of the syringe 3 is filled with a granular bone generation material 10, such as Bioplant®, HTR® bone regeneration material. This barrel is made of either glass or transparent plastic material. The syringe 3 further has the standard plunger 8 on the front end of which is mounted a piston 9. By applying manual pressure to the plunger 8 the piston 9 can be reciprocally slidably axially moved inside the barrel 2 of the syringe 3. The entire assembly, as illustrated in FIG. 2, is mounted inside a non-illustrated conventional blister pack, in which it is distributed to the dentist, surgeon or veterinary practitioner for application of the bone regeneration material to a surgical site. This entire assembly is intended for a single use only and the assembly and blister pack is intended to be discarded after this single use.

Figure 3:
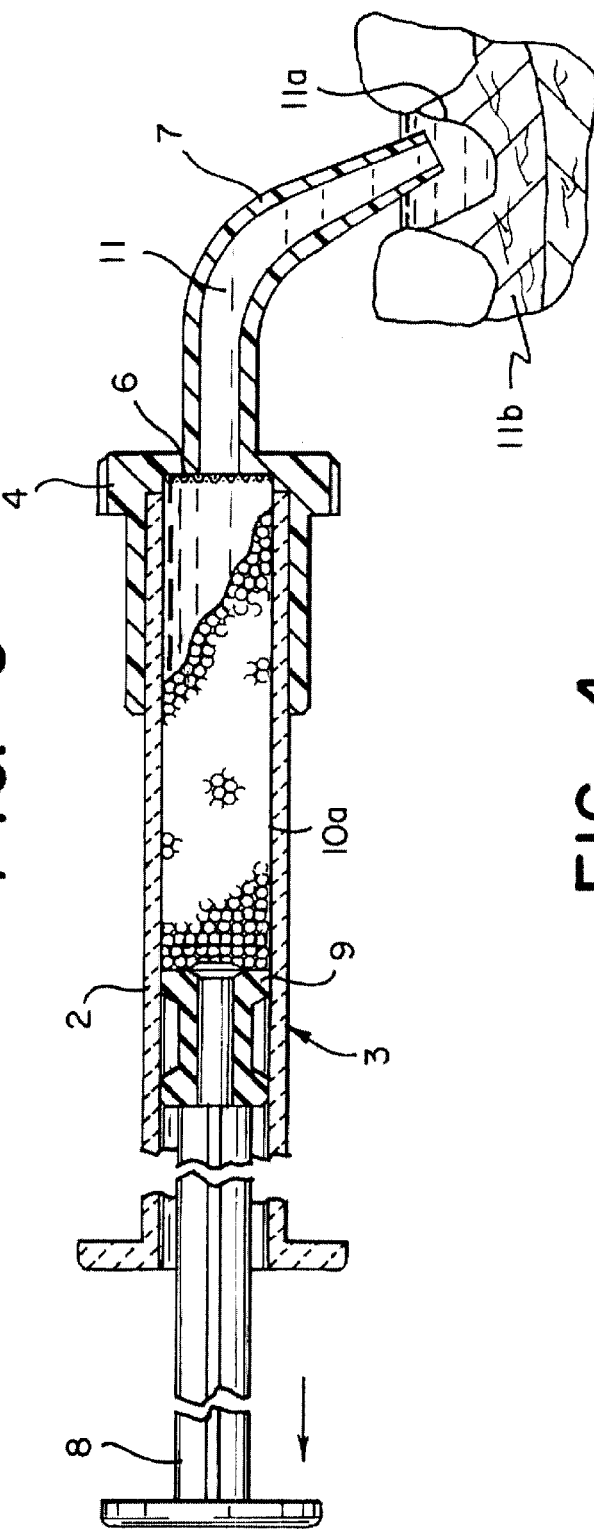
FIG. 3 is a cross-sectional view of the straight barrel syringe of FIG. 2 with the nozzle tip of FIG. 2 mounted thereon during the step of aspirating marrow blood from a tooth socket and mixing it with bone regeneration material in the syringe.

FIGS. 3 and 5 illustrate the aspirating step of the invention using the nozzle tip 1 and syringe 3 of the invention. The curved portion 7b of the nozzle tip 1 is inserted, by way of example, by the dentist into the tooth socket 11a of a jaw bone 11b of a patient immediately after a non-illustrated tooth has been extracted from the tooth socket 11a. Marrow blood 11 is then aspirated through the opening 7c of the neck portion 7 by manually retracting the plunger 8. The aspirated marrow blood 11 flows through neck portion 7 and the screen 6 into the barrel 2 of the syringe where it immediately begins to soak the bone regeneration material 10 with marrow blood 11. By visually examining the syringe 3 the dentist or surgeon determines when a sufficient marrow blood 11 has been aspirated from the tooth socket 11a and has mix with the bone regeneration material 10. If an insufficient a mount of marrow blood has been aspirated the afore-described steps are repeated. If excess marrow blood has been aspirated this excess marrow blood is expelled by slightly manually moving the plunger forward. While these steps are carried out the screen 6 prevents the clogging with granular bone regeneration material of the passage 7d in the straight neck portion 7a of the neck portion 7.

Figure 4:
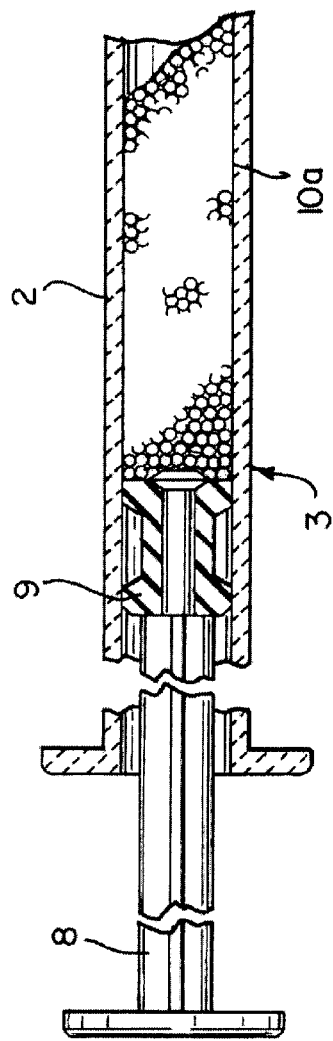
FIG. 4 is a cross-sectional view of the straight barrel syringe of FIG. 2 after the mixing step has been completed and the nozzle tip has been manually removed so that the viscous mass formed by the mixture of marrow blood and bone regeneration material is ready to be applied to a surgical site.

By visually examining the mixture of marrow blood and bone regeneration material inside the syringe barrel 2, the dentist can determine when the mixture 10a of bone regeneration material and marrow blood 11 contains a sufficient amount of marrow blood and thereby the mixture has became sufficiently viscous to be applied to a surgical site. The nozzle tip 1 is then manually slid off the syringe barrel 2 as is shown in FIG. 4.

As is shown in FIG. 6 the viscous mixture 10a is then applied to a surgical site, such as a tooth socket 11a, by applying manual pressure to the plunger 8. Once this step has been completed the surgeon may apply sutures to the surgical site if the surgical condition of the patient warrants such a step.

Although the nozzle tip construction and method of applying a viscous mass of a mixture of marrow blood and bone regeneration material of the present invention have been described in terms of the presently preferred embodiments, it is to be understood that such disclosure is not to be interpreted as limiting. For example, it should be noted that the syringe assembly and method of the invention can be used in other surgical procedures than tooth extraction and can find application in surgery and veterinary medicine. Accordingly, it is intended that the appended claims be interpreted as covering all alterations and modifications as fall within the true spirit and scope of the invention.

What is claimed is:

1. A syringe and nozzle tip assembly for aspirating blood, comprising:
   a) a syringe having a syringe barrel which has a front end and a rear end, said syringe barrel being made of either glass or plastic transparent material;
   b) a piston slidably reciprocally movably mounted in said syringe barrel;
   c) a plunger being connected at its front end to said piston and axially extending rearwardly from said syringe barrel through said rear end thereof; and
   d) a nozzle tip having a flange and a sleeve portion which is coaxially mounted on the front end of said syringe barrel by means of a friction fit; said nozzle tip having a curved neck portion with a passage extending there through for aspirating marrow blood from a surgical site and transporting it into said syringe barrel,
   wherein said nozzle tip flange comprises a surface adapted to seat against the end of syringe barrel when mounted thereon with a recess disposed therein, and a filter mounted in said recess of said flange for preventing the discharge of granular bone regeneration material disposed in said syringe barrel during the step of aspirating the marrow blood.

2. The syringe and nozzle tip assembly as set forth in claim 1, wherein said filter comprises a screen, said screen and curved neck portion are integral with said nozzle tip and said nozzle tip and screen are made of low density polyethylene.

3. The syringe and nozzle tip assembly as set forth in claim 2, wherein the openings of said screen have a mesh size of about 105 microns.

4. A syringe and nozzle tip assembly for aspirating blood, comprising:
   a) a syringe having a syringe barrel which has a front end and a rear end, said syringe barrel being made of either glass or plastic transparent material;
   b) a piston slidably reciprocally movably mounted in said syringe barrel;
   c) a plunger being connected at its front end to said piston and axially extending rearwardly from said syringe barrel through said rear end thereof; and
   d) a nozzle tip having a flange and a sleeve portion which is coaxially mounted on the front end of said syringe barrel solely by means of a friction fit; said nozzle tip having a curved neck portion with a passage extending there through for aspirating marrow blood from a surgical site and transporting it into said syringe barrel,
   wherein said nozzle tip flange comprises a surface adapted to seat against the end of syringe barrel when mounted thereon with a recess disposed therein, and a filter mounted in said recess of said flange for preventing the discharge of granular bone regeneration material disposed in said syringe barrel during the step of aspirating the marrow blood.

5. The syringe and nozzle tip assembly as set forth in claim 1, wherein the outer surface of the syringe barrel is substantially smooth.

6. The syringe and nozzle tip assembly as set forth in claim 1, wherein the recess and filter are configured so that the filter does not contact the end of the syringe barrel.

7. The syringe and nozzle tip assembly as set forth in claim 4, wherein said filter comprises a screen, said screen and curved neck portion are integral with said nozzle tip and said nozzle tip and screen are made of low density polyethylene.

8. The syringe and nozzle tip assembly as set forth in claim 7, wherein the openings of the said screen have a mesh size of about 105 microns.

9. The syringe and nozzle tip assembly as set forth in claim 4, wherein the outer surface of the syringe barrel is substantially smooth.

10. The syringe and nozzle tip assembly as set forth in claim 4, wherein the recess and filter are configured so that the filter does not contact the end of the syringe barrel.

11. The syringe and nozzle tip assembly as set forth in claim 1, wherein the nozzle tip is mounted on the front end of said syringe barrel solely by means of a friction fit.

* * * * *